(12) United States Patent
Kibby et al.

(10) Patent No.: US 6,806,087 B2
(45) Date of Patent: Oct. 19, 2004

(54) USE OF MICROCHANNEL REACTORS IN COMBINATORIAL CHEMISTRY

(75) Inventors: Charles L. Kibby, Benicia, CA (US); Dennis J. O'Rear, Petaluma, CA (US); Georgieanna L. Scheuerman, Moraga, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 29 days.

(21) Appl. No.: 10/156,164

(22) Filed: May 28, 2002

(65) Prior Publication Data

US 2002/0182735 A1 Dec. 5, 2002

Related U.S. Application Data

(63) Continuation of application No. 09/638,325, filed on Aug. 14, 2000, now abandoned.

(51) Int. Cl.[7] .............................................. G01N 31/10
(52) U.S. Cl. ........................ 436/37; 422/129; 422/130; 436/147; 436/155; 436/159
(58) Field of Search ............................ 422/62, 93, 104, 422/129, 130, 196–197; 436/37, 147, 155, 159, 161, 164, 172–173

(56) References Cited

U.S. PATENT DOCUMENTS

| | | | |
|---|---|---|---|
| 2,882,244 A | 4/1959 | Milton | |
| 3,130,007 A | 4/1964 | Breck | |
| 3,216,789 A | 11/1965 | Breck et al. | |
| 3,415,736 A | 12/1968 | Ciric | |
| 3,546,102 A | 12/1970 | Bertolacini | |
| 3,574,092 A | 4/1971 | Mitsche | |
| 3,679,575 A | 7/1972 | Bertolacini | |

(List continued on next page.)

FOREIGN PATENT DOCUMENTS

| | | |
|---|---|---|
| EP | 0 353 915 B1 | 6/1994 |
| GB | 1 117 568 | 6/1968 |

(List continued on next page.)

OTHER PUBLICATIONS

Beck, J. S., et al., "A New Family of Mesoporous Molecular Sieves Prepared with Liquid Crystal Templates", *Reprinted from the Journal of the American Chemical Society*, 1992, vol. 114, No. 27, pp. 10834–10843, Washington, D.C.

(List continued on next page.)

*Primary Examiner*—Arlen Soderquist
(74) *Attorney, Agent, or Firm*—James W. Ambrosius

(57) ABSTRACT

Methods for discovering optimum catalysts and/or reaction conditions for performing endo-or exothermic reactions, in particular gas-to-liquid reactions, are disclosed. A combinatorial approach is used to identify optimum catalysts and/or reaction conditions for performing the reactions. The reactions are performed in the channels of a microchannel reactor. These results can be used directly to optimize large scale reactions performed in a plurality of microchannel reactors, or can be correlated to useful catalysts and reaction conditions for use in large scale reactors by taking into consideration the heat transfer effects in the microchannel reactor and the large scale reactor. The method can advantageously be used to generate a database of combinations of catalyst systems and/or reaction conditions which provide various product streams, such that as market conditions vary and/or product requirements change, conditions suitable for forming desired products can be identified with little or no downtime. The catalysts can be evaluated using varied reaction conditions, which can provide a) a combinatorial library of product streams and a database including the combination of catalysts and reaction conditions to provide each product stream and/or b) the optimum combination of catalysts and reaction conditions for obtaining a desired product stream.

11 Claims, 1 Drawing Sheet

U.S. PATENT DOCUMENTS

| | | |
|---|---|---|
| 3,692,470 A | 9/1972 | Ciric |
| 3,699,035 A | 10/1972 | Hughes et al. |
| 3,709,979 A | 1/1973 | Chu |
| 3,718,576 A | 2/1973 | Hughes et al. |
| 3,726,410 A | 4/1973 | Hughes |
| 3,773,845 A | 11/1973 | Hughes |
| 3,775,505 A | 11/1973 | Hughes |
| 3,793,251 A | 2/1974 | Hughes |
| 3,808,285 A | 4/1974 | Hughes |
| 3,832,449 A | 8/1974 | Rosinski et al. |
| 3,855,876 A | 12/1974 | Burnett |
| RE28,341 E | 2/1975 | Wadlinger et al. |
| 3,864,417 A | 2/1975 | Hughes |
| 3,914,330 A | 10/1975 | Hughes |
| 3,972,983 A | 8/1976 | Ciric |
| 4,016,245 A | 4/1977 | Plank et al. |
| 4,018,711 A | 4/1977 | Bertolacini |
| 4,076,842 A | 2/1978 | Plank et al. |
| 4,104,320 A | 8/1978 | Bernard et al. |
| RE29,948 E | 3/1979 | Dwyer et al. |
| 4,241,036 A | 12/1980 | Flanigen et al. |
| 4,347,394 A | 8/1982 | Detz et al. |
| 4,370,224 A | 1/1983 | Eberly, Jr. et al. |
| 4,417,083 A | 11/1983 | Bernard et al. |
| 4,434,311 A | 2/1984 | Buss et al. |
| 4,447,316 A | 5/1984 | Buss |
| 4,507,517 A | 3/1985 | Devries et al. |
| 4,534,853 A | 8/1985 | Long et al. |
| 4,552,731 A | 11/1985 | Vaughan |
| 4,556,477 A | 12/1985 | Dwyer |
| 4,585,747 A | 4/1986 | Valyocsik |
| 4,599,474 A | 7/1986 | Devries et al. |
| 4,704,487 A | 11/1987 | Devries et al. |
| 4,704,493 A | 11/1987 | Devries et al. |
| 4,709,108 A | 11/1987 | Devries et al. |
| 4,734,537 A | 3/1988 | Devries et al. |
| 4,814,533 A | 3/1989 | Devries et al. |
| 4,814,534 A | 3/1989 | Devries et al. |
| 4,814,538 A | 3/1989 | Devries et al. |
| 4,826,667 A | 5/1989 | Zones et al. |
| 4,834,958 A | 5/1989 | Zones |
| 4,859,442 A | 8/1989 | Zones et al. |
| 4,910,006 A | 3/1990 | Zones et al. |
| 4,963,337 A | 10/1990 | Zones |
| 5,053,373 A | 10/1991 | Zones |
| 5,106,801 A | 4/1992 | Zones et al. |
| 5,198,203 A | 3/1993 | Kresge et al. |
| 5,200,377 A | 4/1993 | Zones et al. |
| 5,202,014 A | 4/1993 | Zones et al. |
| 5,246,689 A | 9/1993 | Beck et al. |
| 5,254,514 A | 10/1993 | Nakagawa |
| 5,316,753 A | 5/1994 | Nakagawa |
| 5,334,368 A | 8/1994 | Beck et al. |
| 5,437,855 A | 8/1995 | Valyocsik |
| 5,559,068 A | 9/1996 | Chen et al. |
| 5,580,540 A | 12/1996 | Nakagawa |
| 5,591,421 A | 1/1997 | Zones |
| 5,624,657 A | 4/1997 | Vaughan |
| 5,811,062 A | 9/1998 | Wegeng et al. |
| 6,063,633 A * | 5/2000 | Willson, III ................ 436/37 |

FOREIGN PATENT DOCUMENTS

| | | | |
|---|---|---|---|
| WO | 97/32208 | * | 9/1997 |
| WO | 99/19724 | * | 4/1999 |
| WO | 00/29844 | * | 5/2000 |

OTHER PUBLICATIONS

Kresge, C. T., et al., "Ordered mesoporous molecular sieves synthesized by a liquid–crystal template mechanism", *Nature, vol. 359, Oct. 22, 1992*, pp. 710–712.

Smits, J. G., "Piezoelectric Micropump with Three Valves Working Peristaltically", *Sensors and Actuators, A21–A23 (1990)*, pp. 203–206. Elsevier Sequoia/Printed in The Netherlands.

* cited by examiner

FIGURE
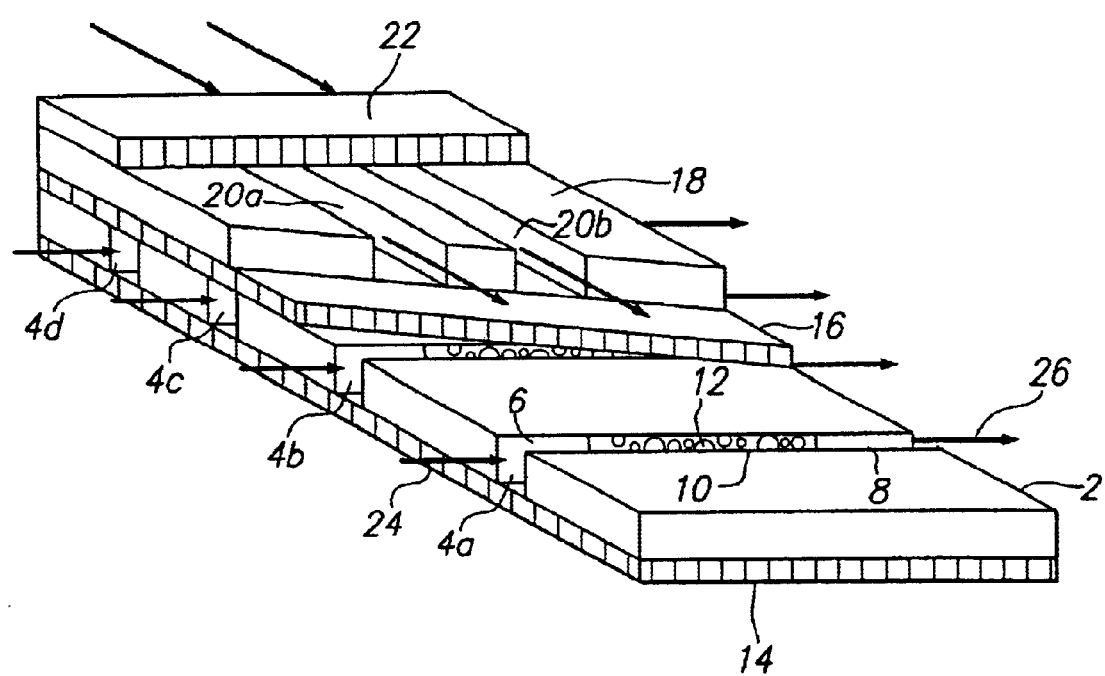

USE OF MICROCHANNEL REACTORS IN COMBINATORIAL CHEMISTRY

CROSS-REFERENCE TO RELATED APPLICATIONS

This application is a continuing application of U.S. patent application Ser. No. 09/638,325 filed on Aug. 14, 2000, now abandoned, the entire contents of which are incorporated herein by reference.

FIELD OF THE INVENTION

This invention is generally in the area of the use of microchannel reactors and/or combinatorial chemistry to optimize the conditions for endo- and exothermic catalytic reactions.

BACKGROUND OF THE INVENTION

Combinatorial chemistry is in widespread use in the pharmaceutical industry, where it is used to synthesize, purify and evaluate new drugs at a tremendously fast pace. In the field of pharmaceutical chemistry, the reactions are typically performed at a relatively small scale, since only a small amount of each drug is required for testing. Typically, only those drugs which are active in relevant bioassays are scaled up. The type of chemistry used to generate commercial quantities of the drugs is rarely the same as that used in small scale synthesis.

Combinatorial chemistry is also being used in petroleum chemistry. However, a major goal in petroleum chemistry is to optimize the reaction conditions and catalysts used for particular reactions rather than to synthesize, purify and evaluate a plurality of products. To have commercial significance, there must be a correlation between the results obtained on the small scale and those which might be obtained on a commercial scale.

One combinatorial chemistry approach used by Symyx to identify optimum catalysts for various reactions involves placing a plurality of catalysts on a metal plate, contacting the plate with a gaseous reactant, and analyzing the products obtained via GC/MS. This approach is limited because, at least for a number of exothermic and endothermic catalytic reactions, it is difficult to correlate the results obtained on this small scale with those obtained on a commercial scale. This limitation exists, in part, because the heat transfer obtained on such a small scale cannot reasonably be correlated with what would be observed in a large reactor.

Heat transfer effects are extremely relevant in exothermic and endothermic reactions. For example, Fischer-Tropsch synthesis, an exothermic reaction, is very sensitive to heat transfer effects. A small scale reaction which provides an acceptable product mixture may provide an unacceptable level of methane production on scale-up due to heat transfer effects. Accordingly, it is often difficult to extrapolate the results on small scale endo- and exothermic reactions to commercial scale reactors. However, it is also difficult to perform combinatorial chemistry using commercial scale reactors.

It would be advantageous to provide devices and methods for discovering optimum catalyst systems using combinatorial chemistry that take the heat transfer effects on product distribution into consideration. The present invention provides such devices and methods.

SUMMARY OF THE INVENTION

The present invention is directed to devices and methods for optimizing endo- and exothermic reactions, in particular, gas-to-liquid reactions, using combinatorial chemistry. The devices include a microchannel reactor that includes a plurality of channels. Some or all of these channels are used to carry out the desired endo- or exothermic reactions. The individual channels include individual catalysts or combinations thereof, such that all or part of a combinatorial library of catalysts can be evaluated. The devices can also include channels which are used to provide heating and cooling, and/or heating and cooling can be provided using other means.

The methods use a combinatorial approach to identify optimum reaction conditions and catalysts or catalyst combinations for performing the desired reactions and/or for providing a desired product. Preferred exothermic reactions are gas-to-liquid reactions, in particular Fischer-Tropsch synthesis, isosynthesis, olefin oligomerization, olefin polymerization, and syngas generation by partial oxidation, methanol synthesis, oxidative methane coupling to ethane and ethylene, methanol conversion to hydrocarbons. Preferred endothermic reactions are catalytic cracking, naphtha reforming, methane conversion to aromatics and steam reforming of methane; steam reforming reaction of $H_2O$ with $CH_4$ to make $H_2$ and CO, with traces of $CO_2$; aromatization, the conversion of paraffins and olefins to aromatics, and hydrocracking reactions. The products can include olefins such as ethylene, iso-paraffins, aromatics and combinations thereof, and preferably include iso-paraffins in the distillate fuel and/or lube base stock ranges, and, more preferably, iso-paraffins in the jet or diesel range.

The methods involve obtaining a microchannel device that includes a plurality of channels, placing an effective amount of a catalyst (or a catalyst combination) from one or more catalyst libraries in a channel, repeating this step as necessary with different channels and different catalysts, and performing the desired reactions. The product streams are preferably analyzed, for example by GC, HPLC and/or GC/MS. The reaction conditions, catalysts, and analytical information regarding the product streams are preferably stored in a database.

The information obtained in the combinatorial step can be applied commercially in several ways. For example, a plurality of microchannel reactors can be used in series and/or in parallel such that the chemistry can be performed on a commercial scale in the plurality of microchannel reactors. This is advantageous, since the reaction conditions and catalysts used in the combinatorial step are directly applicable to the commercial scale chemistry. Alternatively, the results obtained in the microchannel reactors can be correlated to what would be obtained in a conventional large scale reactor.

The microchannel reactors are preferably in the form of a microcomponent sheet architecture, for example a laminate with microchannels. The sheet architecture may be a single laminate with a plurality of separate microcomponent sections or the sheet architecture may be a plurality of laminates with one or more microcomponent sections on each laminate. The microcomponents include passive microcomponents, for example micro flow paths, and active components including but not limited to micropumps and microcompressors. In one embodiment, one type of laminate receives chemical reactants, rejects chemical products and rejects or receives heat to or from a second type of laminate.

The microcomponents or plurality of like microcomponents can perform at least one unit operation. In one embodiment, a first laminate having a plurality of like first microcomponents is combined with at least a second laminate having a plurality of like second microcomponents. The combination of at least two unit operations provides a system operation. For example, a laminate containing a plurality of microchannel evaporators can be combined with an insulating laminate and a laminate containing a plurality of microchannel condensers, and connected to a compressor and expansion valve to obtain a macroscale heat pump. The laminates can be used for chemical processes such as chemical conversions and separations.

Heat transfer in the microchannel reactors is controllable, in part by adjusting the heating/cooling through the microchannels, through the individual laminate layers, and/or through the judicious choice of materials used to prepare the reactors. Ideally, the heating and/or cooling provided by the microchannel reactors can be made to approximate or at least be correlated to that of a large scale (commercial) reactor. One way to provide such a correlation is to place a commercially-known catalyst in one or more of the channels, and adjust the reaction conditions/heating/cooling and other factors such that the results can be correlated with the results obtained in the large scale commercial reactors.

Whether the results obtained in the combinatorial step are used in a plurality of microchannel reactors, or the chemistry is scaled up to a large scale reactor, it may be advantageous to include the same catalyst in a plurality of channels to verify that the results obtained are reasonably consistent throughout the reactor.

The methods can advantageously be used to generate a database of catalysts and, optionally, reaction conditions, which provide various product streams. As market conditions vary and/or product requirements change, conditions suitable for forming desired products can be identified with little or no downtime using the methods described herein.

BRIEF DESCRIPTION OF THE DRAWING

The FIGURE illustrates a section of a microchannel device partially cut away showing the arrangement of four microchannel reactors and two temperature control channels.

DETAILED DESCRIPTION OF THE INVENTION

The present invention is directed to devices and methods for optimizing endo- and exothermic reactions, in particular gas-to-liquid reactions, using combinatorial chemistry. The devices include a microchannel reactor with a plurality of channels, where a plurality of the channels individually include catalysts selected from a library of catalysts. Using the devices and methods described herein, a plurality of catalysts and/or reaction conditions can be evaluated simultaneously.

Types of Reactions

The devices and methods can be used to evaluate and optimize virtually any type of endo- or exothermic catalytic reaction. These types of reactions are well known to those of skill in the art, and include most gas-to-liquid reactions. Particularly preferred gas-to-liquid reactions include Fischer-Tropsch synthesis, isosynthesis (conversion of syngas to methanol and subsequent conversion of the methanol to higher molecular weight products), olefin oligomerization, olefin polymerization, syngas generation by partial oxidation or steam reforming of methane, methanol synthesis, higher alcohol synthesis, oxidative coupling of methane, methane conversion to aromatics, and light paraffin dehydrogenation. Other reactions which can be optimized include hydroformylations, hydrocracking, isodewaxing, isomerizations, dehydrogenations, olefin metathesis, polymerization, paraffin redistribution, alkylbenzene redistribution, molecular redistribution, molecular averaging, naphtha reforming, and catalytic oxidations of various sorts, including CO oxidation, NOx reduction. Molecular averaging and redistribution is described, for example, in U.S. Pat. Nos. 3,699,035; 3,718,576; 3,728,410; 3,773,845; 3,775,505; 3,793,251; 3,808,285; 3,856,876; 3,864,417, and 3,914,330, the contents of which are hereby incorporated by reference.

Reactants

The reactants are typically low molecular weight gases, but can also include liquids. Examples include water, hydrogen gas, carbon monoxide, carbon dioxide, oxygen, syngas (a mixture of carbon monoxide and hydrogen gas), nitrogen oxides (NOx), methane, low molecular weight olefins and/or paraffins (typically including less than 6 carbon atoms), low molecular weight oxygenates such as methanol, ethanol, and dimethyl ether, and other reactive gases. Inert diluent gases may also be present.

The reactants can be reacted with the catalysts in any suitable ratio and amount, given the size of the channels and the desired conversions. The reactants preferably come from a common source, to ensure consistency between channels. A splitter can be used, for example, to direct the reactants to the plurality of channels.

Products

The products are typically light gases and hydrocarbons or oxygenates useful as naphtha, distillate fuels, lube oils, waxes, or as components in such products. The hydrocarbon products generally are olefins such as ethylene, n-paraffins, iso-paraffins, aromatics and combinations thereof, and preferably include iso-paraffins in the distillate fuel and/or lube base stock ranges, and, more preferably, iso-paraffins in the jet or diesel range.

Catalysts

Suitable catalysts for performing various reactions in the field of petroleum chemistry are well known to those of skill in the art. Catalyst libraries including such catalysts and combinations thereof can be readily prepared. Libraries include a plurality of catalysts, preferably at least 10 catalysts, more preferably at least 50 catalysts and most preferably at least 100 catalysts. Large numbers of catalysts can be evaluated, for example by using a plurality of microchannel reactors and/or by performing consecutive runs with a single microchannel reactor.

The amount of the catalyst used in the reaction depends on the size of the channel. Those of skill in the art can readily determine an appropriate amount of catalyst for a particular channel in a microchannel reactor. In gas-to-liquid reactions and a number of other endo- and exothermic reactions, the catalysts tend to be zeolites, other molecular sieves such as borosilicates, ELAPOs such as SAPOs, Fischer-Tropsch catalysts, and alkali or alkaline earth promoted oxides for oxidative coupling of methane and other dehydrogenation reactions, nickel or noble metal catalysts for syngas generation, noble metal catalysts for CO and hydrocarbon oxidation, platinum-based catalysts for naphtha reforming, copper-zinc and zinc-chromium catalysts for methanol synthesis, metal-zeolite catalysts for hydrocracking and hydroisomerization, USY zeolites for catalytic cracking.

Fischer-Tropsch Catalysts

Fischer-Tropsch catalysts contain a Group VIII transition metal on a metal oxide support. The catalysts may also contain a noble metal promoter(s) and/or crystalline molecular sieves. Certain catalysts are known to provide chain growth probabilities that are relatively low to moderate, and the product of the reaction includes a relatively high proportion of low molecular ($C_{2-8}$) weight olefins and a relatively low proportion of high molecular weight ($C_{30}+$) waxes. Certain other catalysts are known to provide relatively high chain growth probabilities. Such catalysts are well known to those of skill in the art and can be readily obtained and/or prepared.

Zeolites

Catalysts useful for isomerizing alpha olefins typically include one or more zeolites and/or non-zeolitic molecular sieves. Those zeolites which are relatively acidic tend to be more efficient than those which are relatively less acidic.

The zeolites and/or molecular sieves are preferably large and/or intermediate pore size zeolites, although zeolites with small pore sizes can be included in the catalyst libraries. Examples of these catalysts, any and all of which can be included in the catalyst libraries, are described, for example, in U.S. Pat. Nos. 3,546,102; 3,574,092; 3,679,575; 4,018,711; 4,104,320; 4,347,394; 4,370,224; 4,417,083; 4,434,311; 4,447,316 and 5,559,068. Zeolite-containing catalysts, for example the zeolite mordenite, ZSM-type zeolites, zeolite L, Faujasites X and Y, and the zeolite omega, are preferably included into the catalyst libraries. L-zeolites and zeolites having an L-zeolite-type channel structure and size, such as ECR-2, which is described in U.S. Pat. No. 4,552,731, and ECR-31, which is described in U.S. Pat. No. 5,624,657 (Vaughan), are also preferably included in the libraries.

The composition of type L-zeolite expressed in terms of mole ratios of oxides may be represented by the following formula:

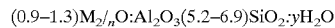

$(0.9–1.3)M_{2/n}O:Al_2O_3(5.2–6.9)SiO_2 \cdot yH_2O$

In the above, formula M represents a cation, n represents the valence of M, and y may be any value from 0 to about 9. Zeolite L, its X-ray diffraction pattern, its properties and method for its preparation are described in detail in, for example, U.S. Pat. No. 3,216,789, the contents of which is hereby incorporated by reference. The actual formula may vary without changing the crystalline structure. For example, the mole ratio of silicon to aluminum (Si/Al) may vary from 1.0 to 3.5.

Examples of useful large pore zeolites include ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44 and MCM-58, any and all of which are preferably incorporated into the libraries. ZSM-3 is described in U.S. Pat. No. 3,415,736. ZSM-4 is described in UK Application No. 1,117,568. ZSM-10 is described in U.S. Pat. No. 3,692,470. ZSM-12 is described in U.S. Pat. No. 3,832,449. ZSM-20 is described in U.S. Pat. No. 3,972,983. Zeolite beta is described in U.S. Pat. No. Re. 28,341 (of original U.S. Pat. No. 3,308,069). Zeolite omega is described in U.S. Pat. No. 4,241,036. Zeolite L is described in U.S. Pat. No. 3,216,789. Zeolite X is described in U.S. Pat. No. 2,882,244. Zeolite Y is described in U.S. Pat. No. 3,130,007. LZ-210, LZ-210M, LZ-210-T, LZ-210-A and mixtures thereof are described in U.S. Pat. No. 4,534,853. SSZ-24 is described in U.S. Pat. No. 4,834,958. SSZ-26 is described in U.S. Pat. No. 4,910,006. SSZ-31 is described in U.S. Pat. No. 5,106,801. SSZ-33 is described in U.S. Pat. No. 4,963,337. SSZ-35 is described in U.S. Pat. No. 5,316,753. SSZ-37 is described in U.S. Pat. No. 5,254,514. SSZ-41 is described in U.S. Pat. No. 5,591,421. SSZ-42 is described in U.S. Ser. No. 08/199,040. SSZ-44 is described in U.S. Pat. No. 5,580,540. MCM-58 is described in U.S. Pat. No. 5,437,855.

Examples of useful intermediate pore size zeolites include ZSM-5, ZSM-11, ZSM-22, ZSM-23, ZSM-35; ZSM-48, ZSM-57, ferrierite, SUZ-4, SSZ-23; SSZ-25; SSZ-28, SSZ-32, and SSZ-36. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application No. 353,915. SSZ-23 is described in U.S. Pat. No. 4,859,442. SSZ-25 is described in U.S. Pat. Nos. 4,826,667 and 5,202,014. SSZ-28 is described in U.S. Pat. No. 5,200,377. SSZ-32 is described in U.S. Pat. No. 5,053,373. The entire contents of all these patents and patent applications are incorporated herein by reference, and any and all of the catalysts described therein can be incorporated into the catalyst libraries. Mesoporous molecular sieves can also be included, for example the M41S family of materials, (J. Am. Chem. Soc., 114:10834–10843 (1992)), MCM-41 (U.S. Pat. Nos. 5,246,689; 5,198,203; 5,334,368) and MCM-48 (Kresge et al., Nature, 359:710 (1992)), the contents of which are hereby incorporated by reference.

Catalyst Supports

Catalysts used in these reactions may be present on a support. Suitable metal oxide supports or matrices which can be used include alumina, titania, silica, magnesium oxide, alkaline earth titanates, alkali titanates, rare earth titanates and mixtures thereof. The catalysts can include any or all of these supports, in varying ratios of weight of support to weight of catalyst.

Typically, the catalysts have a particle size of between 10 and 110 microns, preferably between 20 and 80 microns, more preferably between 25 and 65 microns, and have a density of between 0.25 and 0.9 g/cc, preferably between 0.3 and 0.75 g/cc. The catalysts typically include one or more of the above-mentioned catalytic materials.

Logical Arrays

Libraries of catalysts can be prepared and evaluated using the devices and methods described herein. The identity of the catalyst or combination thereof in each position in the microchannel reactors can be stored in a computerized device, or identified via other identifying means. The products of the reaction can be readily identified, for example by gas chromatography (GC), a combination of gas chromatography and mass spectrometry (GC/MS), infrared heat emissions, infrared species analysis, or UV spectral analysis. To avoid contaminating the columns in chromatographic devices, it may be desirable to filter a representative sample of the product stream before it is placed on the column, for example using an in-line filter or an inline solid phase extraction (SPE) column.

The properties of the reaction products generated during the evaluation of the libraries for a particular chemical reaction can be measured and correlated to specific catalysts, combinations of catalysts, and/or reaction conditions. By screening numerous combinations of catalysts and/or reaction conditions, the selection of the optimal combinations is more a function of the data collection method than the "rational" basis for selecting a useful catalyst and/or set of reaction conditions.

There are several types of reactions in which two or more types of catalysts are used. These catalyst combinations may be used simultaneously or in series, for example in multi-step syntheses. Combinations of catalysts may be used, for example, in multi-step reactions, where one catalyst performs one step and a second catalyst performs a second step. Examples of such reactions include isosynthesis and Fischer-Tropsch synthesis where an acidic catalyst is used to isomerize or isomerize the olefins as they are formed. In such reactions, the optimum overall catalyst combination for producing a desired product may not be the one that includes the optimum catalysts for both steps, since the individual steps may require totally different reaction conditions to be optimized. The overall optimum combination may be one that is the optimum for the first step or for the second step.

For example, the optimum conditions for Fischer-Tropsch synthesis may involve temperatures at a first temperature range, but the optimum olefin isomerization catalysts may operate best at temperatures at a different temperature range. When these Aoptimum@ olefin isomerization catalysts are operated at temperatures in the first temperature range, they may be inefficient. Accordingly, it is preferred that the catalyst combinations include a combination that is optimum for all steps in the multi-step reaction. It is therefore important to test both catalyst components together. However, leads for this screening of optimum catalyst combinations can come from searching the individual catalysts.

When catalyst combinations are used, the catalysts are preferably combined in a logical manner, for example in an A×B array, where each position in the A column includes one or more catalysts for performing the first step of the reaction, and each position in the B row includes one or more catalysts for performing the second step of the reaction. In this manner, virtually every possible combination of catalysts in the libraries can be evaluated. The combinations of catalysts can be evaluated using varied reaction conditions, which can provide a) a combinatorial library of product streams and a database including the combination of catalysts and reaction conditions to provide each product stream and/or b) the optimum combination of catalysts and reaction conditions for obtaining a desired product stream.

Reaction Conditions

The reaction conditions typically involve increased temperature and pressure. Typical pressure ranges are from 10 to 100 bar. Typical temperature ranges are from 100° C. to 1000° C. These conditions may be but need not be the same as those used in large scale commercial reactors. The conditions are expected to be the same as when a plurality of microchannel reactors are used to provide large scale conversions.

A preferred reaction which can be performed in the devices is Fischer-Tropsch synthesis. Examples of catalysts and conditions for performing Fischer-Tropsch type synthesis in fixed and fluidized bed reactors are well known to those of skill in the art, and can be adapted for use in microchannel reactors. Suitable conditions are described, for example, in U.S. Pat. Nos. 4,704,487; 4,507,517; 4,599,474; 4,704,493; 4,709,108; 4,734,537; 4,814,533; 4,814,534 and 4,814,538, the contents of each of which are hereby incorporated by reference in their entirety.

Microchannel Reactors

Any suitable microchannel reactor can be used which can perform a plurality of simultaneous or substantially simultaneous reactions. Such reactors are well known to those of skill in the art and are described, for example, in U.S. Pat. No. 5,811,062 to Wegeng et al., the contents of which are hereby incorporated by reference. The microchannel reactors are capable of performing a plurality of simultaneous or substantially simultaneous reactions which involve gaseous reagents, solid phase catalysts and relatively high temperatures and pressures, although they are also suitable for carrying out other types of reactions as well.

One embodiment of the invention is illustrated by the FIGURE. In this embodiment, a reactor sheet 2 is shown containing four parallel identical microchannel reactors, 4a, 4b, 4c, and 4d, respectively. Each reactor is formed into the reactor sheet as a channel having an inlet 6, an outlet 8, and a reaction zone 10 containing the catalyst 12 which is to be tested. Different catalysts from the library are placed respectively in each microchannel reactor for comparison. Each microchannel reactor is closed on the bottom by a basal laminate 14 and on the top by a heat transfer sheet 16 which are sealed to the reactor sheet 2. A temperature control sheet 18 is sealed to the upper surface of the heat transfer sheet 16 opposite the reactor sheet 2. The temperature control sheet is shown as having two heat transfer fluid channels, 20a and 20b, respectively, which run perpendicular to the microchannel reactors 4a, 4b, 4c, and 4d. The top of the heat transfer fluid channels are closed by an upper laminate 22.

In operation, reactants 24 enter the microchannel reactor 4a via the inlet 6 and pass into the reaction zone 10 where they contact the catalyst 12. The temperature in the reaction zone is controlled by the passage of heat transfer fluids through the heat transfer fluid channels 20a and 20b. By controlling the temperature in each of the heat transfer fluid channels, a temperature gradient may be established within the reaction zone which approximates the temperature gradient observed in a commercial size reactor. The reactants undergo the appropriate reaction under the controlled conditions present in the reaction zone to yield products 26 which exit the microchannel reactor by way of the outlet 8. The performance of the various catalysts in the library under the conditions in the reaction zone may be compared.

Preferably, the reactors include ten or more channels, more preferably greater than 25 channels, most preferably greater than 50 channels. The width W of the grooves or microchannels may range from about 1 micron to about 1 millimeter and preferably range from about 10 microns to about 250 microns.

The voids are an appropriate size for receiving the catalysts used for the endo- or exothermic reactions and for permitting the entry and exit of reactants and products. The microchannel reactors can be prepared from any suitable material, including metals and alloys, polymers, plastics, glass, ceramics, semi-conductors, and the like. They can be formed from a solid material or can be in the form of laminates. The materials must be able to withstand the reaction conditions and also be inert to the catalysts and reactants employed.

Some or all of the channels are used to carry out the desired endo- or exothermic reactions. The individual channels include individual catalysts or combinations thereof, such that all or part of a combinatorial library of catalysts can be evaluated. The devices can also include channels which are used to provide heating and cooling, or heating and cooling can be provided using other means. For example, the reactor can be heated and/or cooled externally and thus heat and/or cool the reactions occurring in the various channels.

Preferably, the reactants are fed to the channels from a single source, for example using a splitter or other suitable means to pass the reactants at approximately the same flow rate to the channels in which the reactions are to occur.

The reactors can be formed from a plurality of laminates. Laminates may comprise material sheets which include a plurality of microcomponents embedded onto one or both sides of the material sheets, material sheets with no microcomponents, or material sheets with conduits through the material sheet thickness serving as a spacer or insulator. The microcomponents can be, for example, condensers, evaporators or non-phase change heat exchangers, compressors, expansion valves, or motors. These examples are not intended to be limiting, and there is practically no limit to the types and numbers of microcomponents and combinations thereof that may be included on a laminate or material sheet. In one embodiment, microcomponents are embedded on both sides of material sheets for use as dual fluid heat exchangers, for example feedwater preheating with condensed turbine exhaust.

The density of microcomponents on a material sheet typically ranges from about 1 microcomponent per square centimeter to about $10^{10}$ microcomponents per square centimeter. Within those density ranges, a range of unit lengths or unit diameters of microcomponents is from about 1 micron to about 1 centimeter.

The microcomponents or groove sets may be embedded into the material sheets by any conventional microchannel forming process, but is preferably done with micromachining or photolithography, with photolithography being particularly preferred. Microchannel forming processes generally etch a surface so that resulting channels are unconfined on the etched side. Channels are closed by bonding a second laminate to the etched surface. A plurality of solid material lands defining a plurality of laterals can be formed to function as heat transfer fins supporting a high heat flux. Each land may be laterally closed or laterally open to permit cross flow communication. The lands may be of any cross section including but not limited to rectangular, rhomboid, and ellipsoid cross sections. Laterally open lands increase flow area thereby reducing the possibility of clogging and reducing the effect of a clog should it occur, and are particularly preferred when solid catalysts are used. In microcomponents with laterally open lands, the definition of a lateral is less distinct, especially if the lands are offset or randomly spaced. Nevertheless, the spaces between the open lands are flow paths.

A single microcomponent or a set of like microcomponents is capable of performing at least one unit operation. A unit operation is defined as an operation that changes the state (thermodynamic state including chemical and/or physical state) of a working fluid, including condensation, evaporation, compression, pumping, heat exchanging, expansion, or chemical process, for example chemical conversion or separation. Chemical reactions may be and preferably are endothermic or exothermic. Conversion reactions include virtually any endo- or exothermic reaction, for example reduction, oxidation, partial oxidation and combustion. Separation involves receiving at least one chemical mixture having a chemical product and a product carrier and separating the chemical product from the product carrier. Examples of separations include distillation, ion exchange and solvent extraction. A collection of unit operations is a system. An example of a single microcomponent performing more than one unit operation is a microcompressor in a thermally conductive material performing both compression and heat transfer simultaneously. Of course, macrocompressors conduct heat as a result of compressing a gas, but that heat is small compared to the process heat, for example heat removed from a refrigerated space. The distinct advantage of a microcomponent is that the heat transferred simultaneous with the compression is indeed process heat, and provides a substantially constant temperature compression (approaching an ideal isothermal compression), which results in efficient energy transfer/conversion. A system may include and preferably does include a microchannel chemical reactor placed upon an microchannel heat exchanger, preferably an evaporator, for temperature control of the chemical reaction thereby permitting control of endo- and exothermic chemical reactions.

In general, a system has a first laminate having a first plurality of microcomponents for performing at least one unit operation, attached to a second laminate having a second plurality of microcomponents for performing at least one additional unit operation. The first unit operation is combined with the additional unit operation and produces a system operation.

Alternatively, instead of having separate unit operations on separate laminates, separate unit operations may be placed on a single laminate having a first portion and at least a second portion. The first portion has first microcomponents for performing a unit operation and the second and subsequent portion(s) have second and subsequent microcomponents for performing another and subsequent unit operation(s). The unit operation is combined with the additional and/or subsequent unit operation(s) and produces a system operation.

Microcomponents performing one unit operation can be combined in several ways with microcomponents performing another unit operation. For example, several microscale pumps in parallel may feed a single heat exchanger, or one microscale pump may feed several heat exchangers in parallel. Similar variations with like microcomponents in series or a combination of series and parallel arrangements may be used advantageously in particular applications.

Laminates or laminate portions are combinable into a wide variety of systems including but not limited to heat pumps, heat engines, heat pipes, thermal sources, and chemical plants, for example chemical converters and chemical separators.

A heat pump of microscale components has the same basic unit operations as a macroscale heat pump. For a vapor compression heat pump, the basic unit operations are evaporation, compression, condensation, and expansion. The microscale components performing each unit operation can provide the same level of macroscale heating or cooling in terms of thermal kilowatts or megawatts as the macroscale counterpart. By adjusting the number of these microscale components, a microchannel reactor can provide roughly the same heat transfer as a large scale reactor.

A heat pump formed of microscale components can include, for example, a microscale evaporator laminate, an insulation laminate, a microscale compressor laminate, and a microscale condenser laminate. The microscale evaporator laminate and condenser laminate are ideally laminates with groove sets, wherein each groove set is a microcomponent. The microscale compressor microcomponent can be a solid piston linear alternator, a piezoelectric diaphragm as described by Smits J G, 1990, "A Piezoelectric Micropump with Three Valves Working Peristaltically", *Sensors and Actuators* 15, 153–67, or other micro-mechanical actuator capable of compressing a gas. Expansion valves or orifices may be etched in the compressor laminate, or a separate laminate containing expansion valves may be inserted between the compressor laminate and the insulation laminate.

The previous description and example of microscale components for a heat pump were centered around a vapor compression cycle. Those skilled in the art of heat pumps would know that other thermodynamic cycles, in addition to vapor compression, are used for heat pumps. For example, Reverse Brayton, Stirling Cycle, and Absorption Cycle have been used.

Thermodynamically, a heat engine is the reverse of a heat pump. However, practically they are quite different. For example, a heat engine does not use an expansion valve, and extracts work from the working fluid. The working fluid may be gas or liquid, but the macroscale heat engine is very different from a macroscale heat pump.

There are numerous thermodynamic cycles upon which even more numerous heat engine designs are based, including but not limited to Rankine Cycle, Brayton Cycle, Stirling Cycle, Otto Cycle, Diesel Cycle, Kalina Cycle, and the Ericcson Cycle. In addition, there are combinations or combined cycles and various energy conservation measures. In the Rankine Cycle, for example, reheat, superheat and feedwater preheating have been used alone or in combination in various heat engine applications. All of these cycles are distinct because of the type of working fluid, internal versus external combustion of fuel, and other characteristics well known to skilled practitioners. Nevertheless, all of these thermodynamic cycles and improvements thereto are the result of attempts to approach the performance of the ideal Carnot Cycle.

Use of microscale laminates, especially condensers and evaporators, have the potential of improving the efficiency of these cycles because of their high specific heat transfer rates.

Distributed production of certain feedstock chemicals, including toxic gases, at their point of use is enabled by the microcomponent sheet architecture in the microchannel reactors. By producing feedstock at the point of use, hazards and expenses of transportation and storage are reduced. Specifically, environmental restoration, particularly groundwater cleanup may involve deployment of a microcomponent sheet architecture chemical process at depth. These steps may also be optimized using combinatorial chemistry.

A microchannel chemical process system is one in which a chemical process unit operation is combined with at least one other unit operation. The use of microchannels for chemical processes permits greater control in the process that cannot be obtained in a conventional "macrochannel" large scale reactor. For example, a broad range of control of temperature is made possible by use of microchannel laminates. Specifically, microchannel chemical reactors used in a sheet architecture permit controlled temperature gradients or controlled temperature variation across a sheet of microchannels thereby permitting quenching and attainment of non-equilibrium states. In addition to temperature, other parameters may be closely controlled. Specifically, microchannel geometry is useful for control of residence time, or velocity profile or both. Energy other than thermal energy may be used to activate a reaction or to otherwise create an environment conducive to specific desired reactions, including electrical field induced reactions (e.g., plasmas or aqueous phase electrochemical reactors) magnetically induced or controlled chemical reactions and sonically induced reactions. An example of providing a temperature gradient is having a sheet of parallel microchannels for a condenser or evaporator wherein adjacent microchannels are held at different pressures, thereby experiencing phase change at different temperatures. With a reactor sheet having microchannels positioned in crossflow with respect to the condenser or evaporator microchannels, the reactions conditions are controllable along the length of the microchannel reactor.

Because microchannel reactors are typically used for reactions that do not require materials or solids that would clog the microchannels and that do not produce materials or solids that would clog the microchannel (see, for example, U.S. Pat. No. 5,8111,062), the size of the voids must be adjusted to account for the use of solid catalysts. One approach is to coat the voids with a coating of a catalyst, rather than to fill the voids with solid catalyst. Because the microchannel sheet architecture is capable of precise and accurate control of localized reaction conditions, for example reaction temperature and temperature gradient control at predetermined reactor location(s), it is preferred that the microchannel sheet architecture be used for reactions wherein precise control is beneficial.

Control of reaction temperature is critical for all endo- and exothermic reactions and control of residence time may be critical depending upon the reaction and reaction conditions. For example, partial oxidation of methane to hydrogen requires both control of temperature and residence time to avoid combustion of methane to carbon dioxide and water. By placing a sheet of microchannels for reaction on a sheet of microchannels for cooling, the reaction temperature is controllable to maximize yield of hydrogen.

Temperature control may be achieved in any of several ways. For example, when a first sheet or laminate is in a cross flow relationship to a second sheet or laminate, a temperature gradient along a flow direction of the first laminate is maintained by controlling temperature of coolant within particular microchannels or microcomponents. When two-phase flow is used in the heat transfer sheet or laminate, pressure would be used to control phase change temperature. Alternatively, geometry of the microchannels, e.g., variable flow path width, cross sectional area and/or shape may be used to optimize heat transfer to or from a chemical process sheet or laminate.

In one embodiment, at least a portion of the channels are used to separate products from reactants. Chemical separations, as used herein, include any exchange of a compound or element from one solvent to another where the solvents may be liquid or gas or both. An example is an absorption cycle refrigeration system. In chemical separations, a porous membrane is used that is selected so that a first solvent containing the element or compound does not wet the porous membrane but a second solvent wets the porous membrane and the element or compound in the first solvent transfers to the second solvent through the porous membrane.

By making the depths of the solvents small, i.e., less than about 100 microns, higher absorption rates are achieved than with larger depths. A microporous contactor unit is a microporous contactor sheet placed between cover sheets. Each cover sheet has a microplenum or at least one microcomponent together with an inlet and an outlet permitting fluid flow across the microporous contactor sheet.

In most practical systems, to achieve high absorption/desorption rates, heat will need to be transferred either to or from the absorption/desorption fluids. Accordingly, a heat transfer sheet as previously described may be combined with the microporous contactor unit.

The pores are preferably as small as practical, on the order of a few microns, i.e., less than about 10 microns, and most preferably less than about 3 microns. The small pore size provides a strong resistance to a through-sheet velocity or pressure gradient. A cover is placed over the sheet having a fluid plenum that is less than about 10 microns in height from the sheet to the cover. Mass diffusion then occurs within a stagnant film and through the microporous contactor sheet. Micro-components may be manufactured on one or both sides of the microporous contactor sheet. Additionally, the microporous contactor sheet may have no microcomponents itself, but the cover sheet(s) may have microcomponents for directing fluid flow across the microporous contactor sheet. A further embodiment is simply a fluid microplenum on either side of the microporous contactor sheet.

The microporous contactor sheet may be made by micromachining a metal, ceramic or plastic by, for example, lithography, preferably photolithography, electrodeposition, injection molding, or sintering. Advantages of micromachined contactor sheets include precise control of the pore size throughout the sheet.

In operation, fluids may flow in parallel, counterflow or crossflow. The parallel flow results in lesser mass flux or extraction, but permits lesser pressure differential or gradient across the microporous sheet. When gas is one of the fluids and the gas is to be absorbed into a liquid, it is preferred that the gas pass through the microporous sheet but not the liquid. Accordingly, it is preferred that the microporous sheet either be coated so that the liquid does not wet the microporous sheet or have pores sufficiently small so that the liquid is supported by its surface tension and does not flow through the pores.

In the case wherein a microporous sheet is not sufficiently self supporting between the covers, the covers may be made with projections or lands for support of the microporous sheet. Alternatively, as previously discussed, the microporous sheet may have grooves or microcomponents. In either case, projections or lands would support the microporous sheet.

Analytical Equipment

The products from the reactions are preferably analyzed after they pass through the individual channels. Suitable analytical equipment for analyzing the products of chemical reactions, particularly reactions common to petroleum chemistry, are well known to those of skill in the art.

After the chemical reactions takes place, the reaction products can be individually transferred from the individual channels to an analytical device. Any device that can take samples from the individual channels in the reactors and analyze the resulting compounds can be used.

The analytical device is a preferably chromatographic device such as an analytical or preparative scale HPLC, GC or GC/MS, although other devices can be envisioned, depending on the chemistry performed. Since the product streams may not include UV-active compounds, the analytical equipment preferably includes an ELSD detector or other detector which is not dependent on UV absorption to detect a compound eluting from the column.

Particularly when iso-paraffin concentration is evaluated using the library, a combination of GC and MS is used. Isomers tend to have the same MS peaks, but elute at different times from the columns, and this technique allows rapid determination of the product stream.

The products can be assayed for various properties including octane and/or cetane values, degree of isomerization, olefin concentration, and the like. Preferably the products are analyzed in a high-throughput manner. Conditions are known in the art for determining the octane or cetane values based on known GC data, when a GC is performed on a representative sample of the product stream. These techniques may be particularly useful in evaluating the libraries for useful catalyst combinations for preparing products with desirable properties.

Using information obtained in the analyses, those of skill in the art can readily optimize the reactions by varying various process conditions, for example reagent composition, temperature, pressure, flow rate and the like.

Database

Data regarding the catalysts or combinations thereof, reaction conditions and product streams can be stored in a relational database. The database can be used to find optimum catalyst combinations for producing a desired product stream, and can be particularly useful when the desired product stream varies depending on market factors. When the product requirements change, appropriate catalysts and/or reaction conditions can be selected to prepare the desired product.

The data is preferably stored in a computer system capable of storing information regarding the identity of the catalysts and the product streams obtained, particularly when a plurality of different reaction conditions are used. Software for managing the data is stored on the computer. Relational database software can be used to correlate the identity of the ionic liquids, the reaction conditions (for example reagent composition, temperature and pressure) and the analytical data from each product stream. Numerous commercially available relational database software programs are available, for example from Oracle, Tripos, MDL, Oxford Molecular ("Chemical Design"), IDBS ("Activity Base") and other software vendors.

Relational database software is a preferred type of software for managing the data obtained during the processes described herein. However, any software that is able to create a "memory map" of the catalysts in the reaction vessels and correlate that information with the information obtained from the chemical reactions can be used. This type of software is well known to those of skill in the art.

Library Design

Software for the design of test libraries can be used to design the original catalyst test libraries based on input from literature and previous experimental programs. This software can be used to efficiently design test libraries which cover the desired experimental space and utilize statistical experimental design methods.

Other software can be used to analyze the data from experiments and correlate that data with the structure of the catalysts and/or catalyst treatment conditions and/or reaction conditions. Such correlations are often referred to as SAR software (Structure Activity Relations). Such SAR can then be used by the software to design subsequent catalyst test libraries for further screening. The use of such SAR programs can add to the efficiency of screening. As more data is collected, these SAR programs can become more efficient at developing catalyst libraries with increased probability for finding desirable catalysts.

Methods

The methods use a combinatorial approach to identify optimum reaction conditions and catalysts or catalyst combinations for performing the desired reactions and/or for providing a desired product. The methods involve obtaining a microchannel device that includes a plurality of channels, placing an effective amount of a catalyst (or a catalyst combination) from one or more catalyst libraries in a channel, repeating this step as necessary with different channels and different catalysts so that a plurality of catalysts can be simultaneously evaluated, and performing the desired reactions. The product streams are then preferably analyzed, more preferably by GC, HPLC or GC/MS. The reaction conditions, catalysts, and analytical information regarding the product streams are preferably stored in a database.

In one embodiment, the results are used to determine optimum conditions for performing larger scale reactions using a plurality of microchannel devices. In this embodiment, the results from the combinatorial chemistry are directly applicable to the large scale synthesis.

In another embodiment, the results obtained using the microchannel devices can be correlated with what would occur in a large scale commercial reactor. The microchannel reactors can generate information regarding a large number of catalysts and reaction conditions, which is then used to design optimum conditions for running large scale reactions in commercial reactors. In this embodiment, the heat transfer effects in the microchannel reactors must be correlated with that observed in the large scale reactors.

The heating and/or cooling provided by the microchannel reactors can be adjusted to approximate or at least can be correlated to that of a large scale (commercial) reactor. One way to provide such a correlation is to place a commercially known catalyst in one or more of the channels, and adjusting the reaction conditions and heating/cooling such that the results can be correlated with the results obtained commercially.

In either embodiment, it is preferred that the same catalyst is placed in a plurality of channels to verify that the results obtained are reasonably consistent throughout the reactor.

The methods can advantageously be used to generate a database of catalysts and, optionally, reaction conditions, which provide various product streams. As market conditions vary and/or product requirements change, conditions suitable for forming desired products can be identified with little or no downtime using the methods described herein.

While preferred embodiments of the present invention have been shown and described, it will be apparent to those skilled in the art that many changes and modifications may be made without departing from the invention in its broader aspects. The skilled person would be able to apply pre-heating, intercooling, re-heating, combined cycles, chemical process unit operation(s) and other variations as has been done in macro systems. The appended claims are therefore intended to cover all such changes and modifications as fall within the true spirit and scope of the invention.

We claim:

1. A method for discovering optimum systems and/or reaction conditions for carrying out endo- or exothermic reactions, which comprises:

a) preparing a library of catalysts for carrying out the desired reaction, b) placing a catalyst from the library in a microchannel chemical reactor of a microchannel device containing a plurality of microchannel chemical reactors, said microchannel device further having a microchannel heat exchanger which is so disposed to provide means for controlling the temperature and establishing a predetermined temperature gradient within each microchannel chemical reactor, c) repeating step b until a desired number of catalysts have been placed in a desired number of microchannel chemical reactors, d) feeding reactants to the microchannel chemical reactors containing catalysts under conditions which cause the reactants to be converted into products, e) analyzing the products in order to collect data on the performance of each catalyst under the reaction conditions in each microchannel chemical reactor, and f) evaluating the data to identify the optimal catalyst and reaction conditions.

2. The method of claim 1, wherein the catalyst comprise Fischer-Tropsch catalysts.

3. The method of claim 1, wherein the catalysts zeolite catalysts.

4. The method of claim 1, wherein the catalysts dehydrogenation catalysts.

5. The method of claim 1, further comprising storing information regarding the identity of the catalysts and their position in the microchannel reactor.

6. The method of claim 1, further comprising storing information regarding the analysis of the reaction products in a database.

7. The method of claim 1, wherein step d is repeated at least one time using different reaction conditions.

8. The process of claim 7, wherein the reaction conditions which are varied are selected from the group consisting of temperature, pressure, reactant composition, and flow rate.

9. The method of claim 1, wherein the products include iso-paraffin in the jet fuel range.

10. The method of claim 1, wherein the products include iso-paraffin in the diesel fuel range.

11. The method of claim 1, wherein the products include iso-paraffin in the lube base oil range.

* * * * *